US010113992B2

(12) United States Patent
Toudou et al.

(10) Patent No.: US 10,113,992 B2
(45) Date of Patent: Oct. 30, 2018

(54) GAS CONCENTRATION MEASURING APPARATUS

(71) Applicant: DENSO CORPORATION, Kariya, Aichi-pref. (JP)

(72) Inventors: Yuusuke Toudou, Kariya (JP); Takehito Kimata, Kariya (JP); Toru Katafuchi, Kariya (JP)

(73) Assignee: DENSO CORPORATION, Kariya (JP)

( * ) Notice: Subject to any disclaimer, the term of this patent is extended or adjusted under 35 U.S.C. 154(b) by 0 days.

(21) Appl. No.: 15/947,037

(22) Filed: Apr. 6, 2018

(65) Prior Publication Data
US 2018/0224396 A1    Aug. 9, 2018

Related U.S. Application Data

(62) Division of application No. 14/914,370, filed as application No. PCT/JP2014/072719 on Aug. 29, 2014.

(30) Foreign Application Priority Data

Aug. 30, 2013  (JP) ................................ 2013-178980
Aug. 18, 2014  (JP) ................................ 2014-165752

(51) Int. Cl.
*G01N 27/407*  (2006.01)
*G01N 27/417*  (2006.01)
*G01N 27/419*  (2006.01)

(52) U.S. Cl.
CPC ....... *G01N 27/4175* (2013.01); *G01N 27/407* (2013.01); *G01N 27/419* (2013.01)

(58) Field of Classification Search
CPC . G01N 27/4175; G01N 27/407; G01N 27/419
See application file for complete search history.

(56) References Cited

U.S. PATENT DOCUMENTS 6,295,862 B1 * 10/2001  Kurokawa ........... G01N 27/417
                                                                204/410
6,551,497 B1    4/2003  Gao et al.
(Continued)

FOREIGN PATENT DOCUMENTS

JP        63-63964     3/1988
JP        10-206363    8/1998
(Continued)

OTHER PUBLICATIONS

International Search Report for PCT/JP2014/072719, dated Nov. 11, 2014, 4 pages.
(Continued)

*Primary Examiner* — Susan D Leong
(74) *Attorney, Agent, or Firm* — Nixon & Vanderhye P.C.

(57) ABSTRACT

A gas concentration measuring apparatus is provided which works to calculate the concentration of a given gas component with enhanced accuracy. The gas concentration measuring apparatus 1 includes, a gas sensor 10 and a calculating portion 11. The gas sensor 10 is equipped with a pump cell 3, a monitor cell 4, and a sensor cell 5. The calculating portion 11 subtracts a monitor cell current Im that is a current flowing through the monitor cell 4 from a sensor cell current Is that is a current flowing through the sensor cell 5 to calculate the concentration of the given gas component in gas g. When calculating the concentration of the given gas component, the calculating portion 11 performs a correction operation to bring a value of the monitor cell current Im close to a value of an oxygen dependent current Iso that is a component of the sensor cell current Is which arises from the concentration of oxygen.

5 Claims, 13 Drawing Sheets

(56) References Cited

U.S. PATENT DOCUMENTS

| | | | |
|---|---|---|---|
| 2001/0039825 A1* | 11/2001 | Kurokawa | G01N 27/417 73/31.05 |
| 2002/0050455 A1* | 5/2002 | Kurokawa | G01N 27/4175 204/431 |
| 2002/0104758 A1 | 8/2002 | Mizutani et al. | |
| 2002/0195338 A1 | 12/2002 | Mizutani et al. | |
| 2004/0050695 A1 | 3/2004 | Haraguchi et al. | |
| 2009/0236223 A1 | 9/2009 | Hada et al. | |
| 2009/0242427 A1 | 10/2009 | Muroguchi et al. | |
| 2013/0180854 A1 | 7/2013 | Sasaki | |

FOREIGN PATENT DOCUMENTS

| | | |
|---|---|---|
| JP | 2000-321238 | 11/2000 |
| JP | 2002-310987 | 10/2002 |
| JP | 2003-083936 | 3/2003 |
| JP | 3979240 | 9/2007 |
| JP | 2009-229148 | 10/2009 |
| JP | 2009-244048 | 10/2009 |
| JP | 2011-58834 | 3/2011 |
| JP | 2013-148358 | 8/2013 |

OTHER PUBLICATIONS

Written Opinion of the ISA for PCT/JP2014/072719, dated Nov. 11, 2014, 4 pages.

\* cited by examiner

NOT CONTAINING NOx

CORRELATION BETWEEN SENSOR CELL CURRENT AND MONITOR CELL CURRENT

GAS CONCENTRATION MEASURING APPARATUS

This is a divisional of U.S. application Ser. No. 14/914,370, filed Feb. 25, 2016, which is the U.S. national phase of International Application No. PCT/JP2014/072719 filed Aug. 29, 2014 which designated the U.S. and claims priority to JP Patent Application No. 2013-178980 filed Aug. 30, 2013 and JP Patent Application No. 2014-165752 filed Aug. 18, 2014, the entire contents of each of which are hereby incorporated by reference.

TECHNICAL FIELD

The present invention generally relates to a gas concentration measuring apparatus which works to measure the concentration of a gas component such as NOx contained in exhaust gas from automotive vehicles.

BACKGROUND ART

A gas measuring apparatus which is equipped with a gas sensor exposed to exhaust gas from an automotive vehicle and a calculating portion which uses an output of the gas sensor to calculate the concentration of NOx contained in the exhaust gas (see Patent Literature 1, as listed below).

The gas sensor is equipped with a solid electrolyte body which has oxygen ion conductivity and a plurality of electrodes formed on both surfaces of the solid electrolyte body. The solid electrolyte body and the electrodes form three cells: a pump cell, a monitor cell, and a sensor cell. The pump cell is a cell which reduces the concentration of gas. The monitor cell is a cell which detects the concentration of oxygen slightly remaining in the gas whose concentration of oxygen has been reduced by the pump cell. The sensor cell is a cell which measures the sum of concentrations of oxygen and a given gas component (NOx) contained in the gas whose concentration of oxygen has been reduced by the pump cell.

An amount of electric current (i.e., a monitor cell current Im) which corresponds to the concentration of oxygen remaining in the gas flows through the monitor cell. An electric current (i.e., a sensor cell current Is) also flows through the sensor cell. The sensor cell is active both to oxygen and to the given gas component. The sensor cell current Is, therefore, includes a component (i.e., an oxygen dependent current Iso) arising from the concentration of oxygen and a component (i.e., a given gas dependent current Ix) arising from the concentration of the given gas component. The accurate determination of the concentration of the given gas component required elimination of the oxygen dependent current Iso from the sensor cell current Is to precisely derive the given gas dependent current Ix.

It is, however, usually impossible to directly measure the oxygen dependent current Iso. The above gas concentration measuring apparatus, therefore, uses the monitor cell current Im instead of the oxygen dependent current Iso. Specifically, the monitor cell current Im, like the oxygen dependent current Iso, has a correlation with the concentration of oxygen. The monitor cell current Im is, thus, subtracted from the sensor cell current Is(=Iso+Ix) to obtain an approximate value of the given gas dependent current Ix. The approximate value is used to calculate the concentration of the given gas component. This operation is made by the above calculating portion.

CITATION LIST

Patent Literature

PATENT LITERATURE 1 Japanese Patent No. 3979240

SUMMARY OF THE INVENTION

Problem to be Solved by the Invention

It, however, may be impossible for the above gas measuring apparatus to accurately measure the concentration of the given gas component. Specifically, the electrode constituting the monitor cell is made of metal, for example, Pt—Au alloy which reduces only oxygen molecules. The electrode making the sensor cell is made of metal, for example, Pt—Rh alloy which reduces both the oxygen molecules and the given gas component. The monitor cell and the sensor cell are different in material of the electrodes from each other and thus different in sensitivity to the concentration of oxygen from each other. Additionally, there is also a manufacturing variation in area of the electrodes. This may result in a difference between the monitor cell current Im and the oxygen dependent current Iso, which leads to a difficulty in subtracting the monitor cell current Im from the sensor cell current Is(=Ix+Iso) to accurately calculate the given gas dependent current Ix for determining the concentration of the given gas component.

The invention was made against such a background and provides a gas concentration measuring apparatus which is capable of determining the concentration of the given gas component with enhanced accuracy.

Means For Solving the Problem

One aspect of the invention is a gas concentration measuring apparatus which comprises a gas sensor exposed to gas and a calculating portion which uses an output from the gas sensor to calculate a concentration of a given gas component contained in the gas, characterized in that the gas sensor includes a gas chamber into which the gas is introduced, a reference gas chamber into which a reference gas is introduced, a solid electrolyte body which is disposed between the gas chamber and the reference gas chamber and has oxygen ion conductivity, and a plurality of electrodes disposed on both surfaces of the solid electrolyte body, in that the solid electrolyte body and the electrodes constitute a pump cell which works to regulate an oxygen concentration of the gas in the gas chamber, a monitor cell through which an amount of current corresponding to the oxygen concentration of the gas flows, and a sensor cell through which a current that is the sum of an amount of current corresponding to the oxygen concentration and an amount of current corresponding to a concentration of the given gas component in the gas flows, in that the calculating portion works to correct a value of a monitor cell current Im that is the current flowing through the monitor cell to bring it close to a value of an oxygen dependent current Iso which is a component of a sensor cell current Is that is the current flowing through the sensor cell and which arises from a concentration of oxygen, and also subtract a corrected value Im' thereof from the sensor cell current Is to determine a given gas dependent current Ix that is a component of the sensor cell current Is which arises from the concentration of the given gas component to calculate the concentration of the given gas component in the gas.

Effect of the Invention

The calculating portion of the gas concentration measuring apparatus works to correct the monitor cell current Im to bring it close to the oxygen dependent current Iso when determining the concentration of the given gas component. This enhances the accuracy in calculating the concentration of the given gas component. Specifically, the sensor cell current Is, as described above, includes the given gas dependent current Ix that is a component arising from the concentration of the given gas component and the oxygen dependent current Iso. The above correction operation is, therefore, made to approximate the monitor cell current Im' after being corrected to the oxygen dependent current Iso. Subtraction of the monitor cell current Im' from the sensor cell current Is(=Ix+Iso), thus, derives a relation of Is−Im'= (Ix+Iso)−Im'≈Ix, which enables the given gas dependent current Ix to be calculated accurately. This results in an enhanced accuracy in determining the concentration of the given gas component.

The present invention, as described above, provides the gas concentration measuring apparatus which is capable of calculating the concentration of the given gas component with enhanced accuracy.

EMBODIMENT FOR CARRYING OUT THE INVENTION

Figure 1:
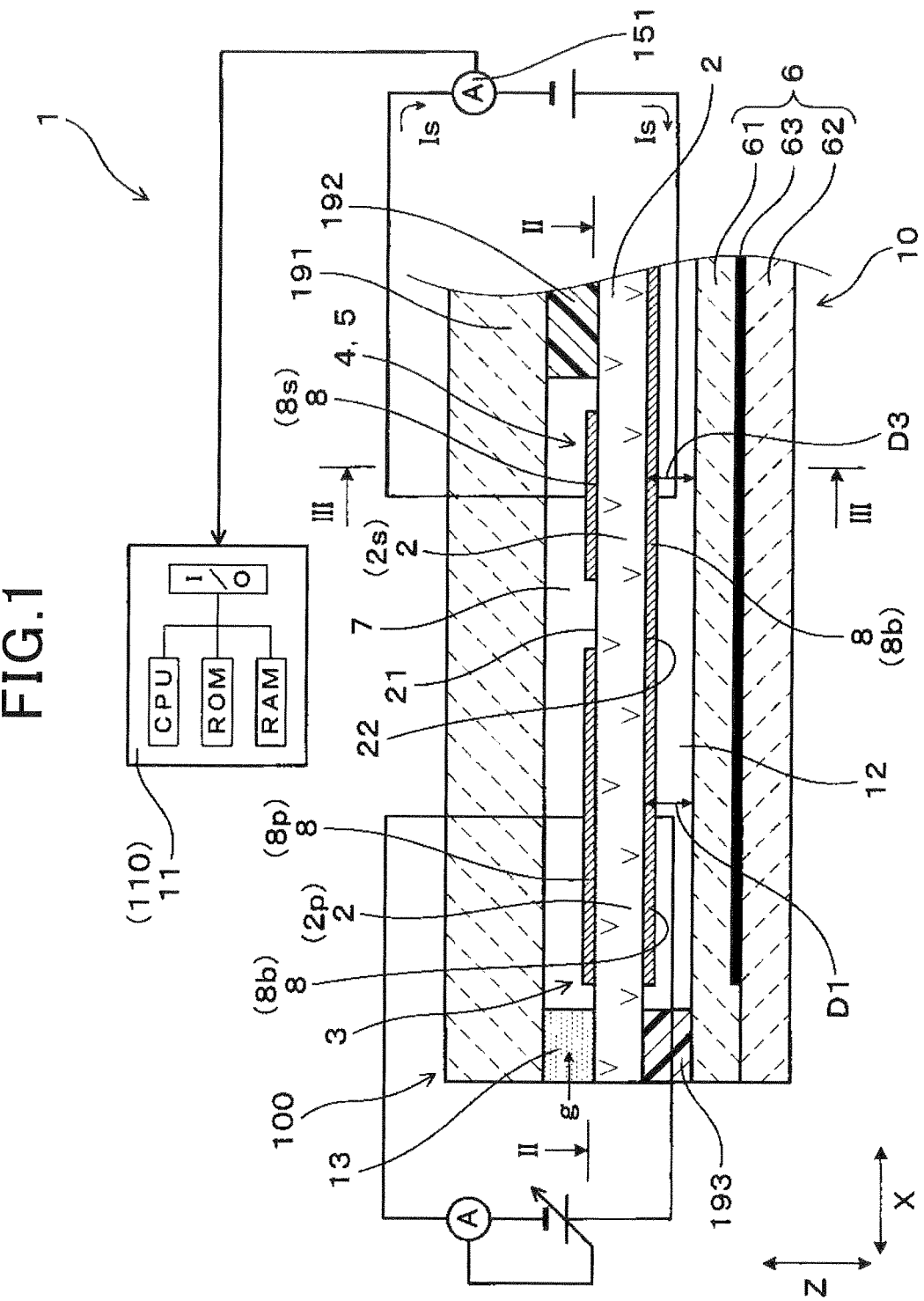
FIG. 1 is a sectional view of a gas sensor in the first embodiment.

The above described gas concentration measuring apparatus may be designed as, for example, a NOx concentration measuring apparatus which measures the concentration of NOx contained in exhaust emissions from automotive vehicles.

Embodiment

Embodiment 1

An embodiment of the above gas concentration measuring apparatus will be explained using FIGS. 1 to 11. The gas concentration measuring apparatus 1 of this embodiment is, as illustrated in FIGS. 1 to 4, equipped with a gas sensor 10 and a calculating portion 11. The gas sensor 10 has the top end 100 exposed to the gas g. The calculating portion 11 uses an output current from the gas sensor 10 to calculate the concentration of a gas component contained in the gas g.

The gas sensor 10 includes a gas chamber 7, a reference gas chamber 12, a solid electrolyte body 2, and a plurality of electrodes 8. The gas g is admitted into the gas chamber 7. A reference gas such as atmospheric air is admitted into the reference gas chamber 7. The solid electrolyte body 2 is interposed between the gas chamber 7 and the reference gas chamber 12. The solid electrolyte body 2 is made from material having oxygen ion conductivity. The electrodes 8 are formed on both surfaces of the solid electrolyte body 2.

Figure 2:
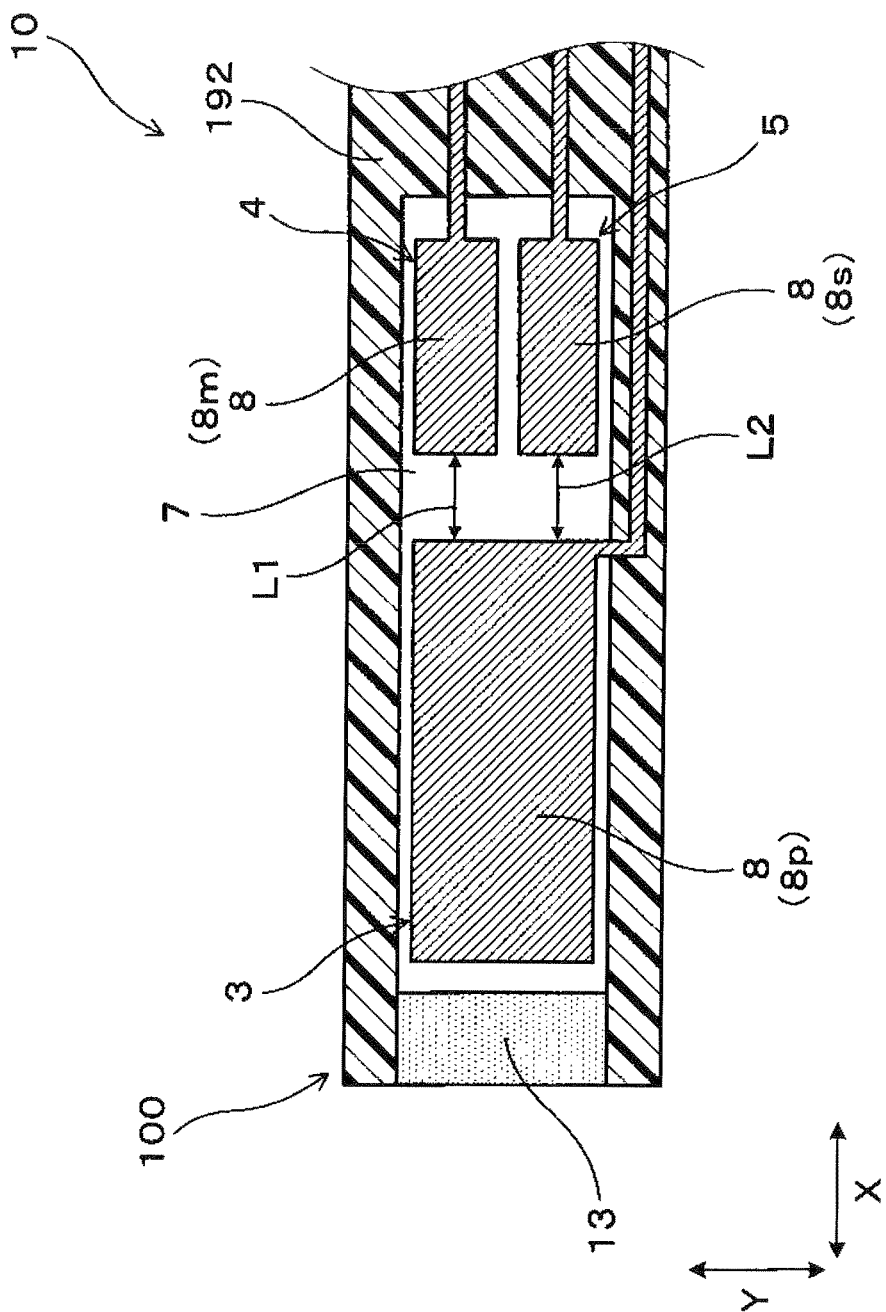
FIG. 2 is a II-II sectional view in FIG. 1.
Figure 3:
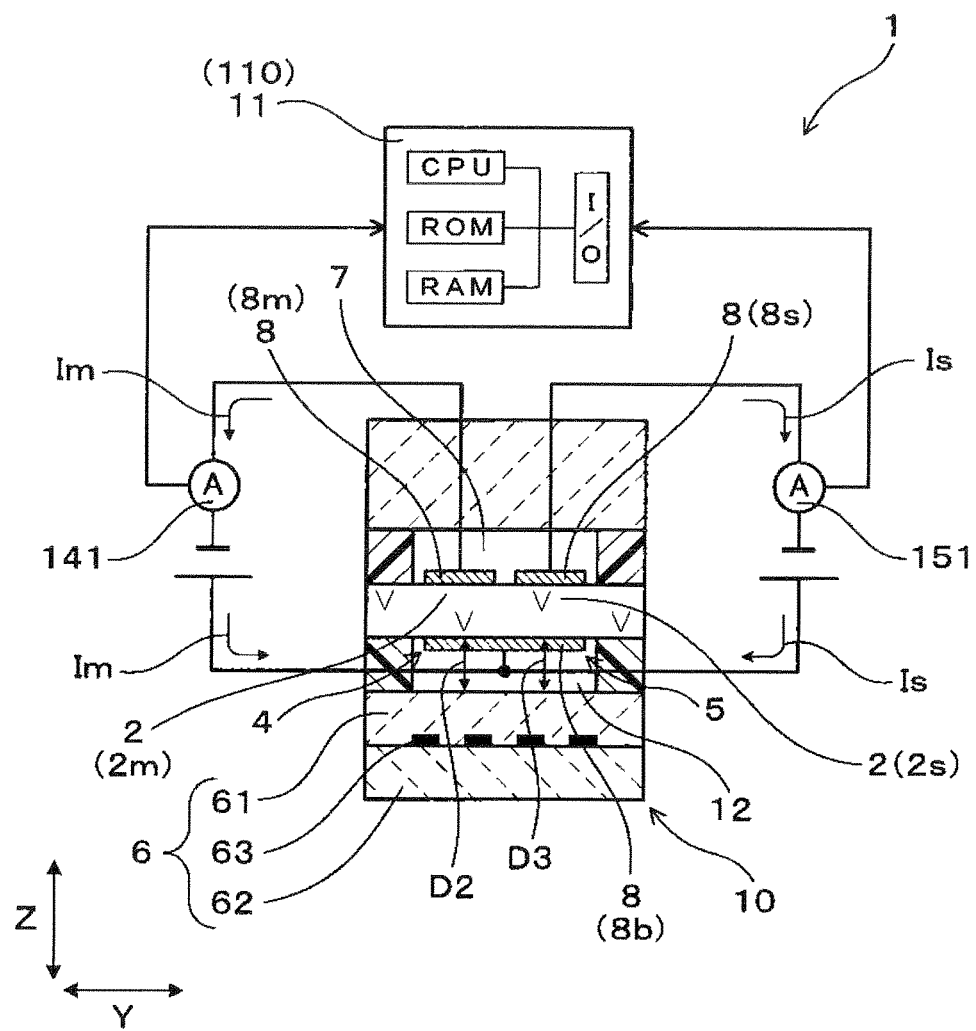
FIG. 3 is a III-III sectional view in FIG. 1.

The solid electrolyte body 2 and the electrodes 8, as illustrated in FIGS. 1 to 3, form a pump cell 3, a monitor cell 4, and a sensor cell 5. The pump cell 3 is a cell working to regulate the concentration of oxygen in the gas g within the gas chamber 7. The monitor cell 4 is a cell through which an electric current flows as a function of the concentration of oxygen in the gas g. The sensor cell 5 is a cell through which the sum of an amount of current corresponding to the concentration of oxygen in the gas g and an amount of current corresponding to the concentration of a given gas component in the gas g flows.

The monitor cell current Im flows through the monitor cell 4. The sensor cell current Is flows through the sensor cell 5. The sensor cell current Is includes an oxygen dependent current Iso that is a component developed by the concentration of oxygen and a given gas dependent current Ix that is a component developed by the concentration of the given gas component (see FIG. 6). The calculating portion 11 works to perform a correction operation to bring the value of the monitor cell current Im close to the value of the oxygen dependent current Iso. The value of the corrected monitor cell current Im' is subtracted from the sensor cell current Is to derive the given gas dependent current Ix. The value of the given gas dependent current Ix is used to calculate the concentration of the given gas component contained in the gas g.

The gas concentration measuring apparatus 1 of this embodiment is a NOx concentration measuring apparatus designed to measure the concentration of NOx contained in exhaust gas from an automotive vehicle. Specifically, the gas g is the exhaust gas from the automotive vehicle. The given gas component is NOx. The whole of the gas sensor 10 is installed in a cylindrical case, not shown, and installed in an exhaust pipe of the automotive vehicle. The top end 100 of the gas sensor 10 is inserted into the exhaust pipe, while the rear end thereof is exposed to atmospheric air.

The electrode 8, as illustrated in FIGS. 1 to 4, includes a pump electrode 8p, a monitor electrode 8m, and a sensor electrode 8s which are formed on a major surface 21 of the solid electrolyte body 2 facing the gas chamber 7 and a reference electrode 8b which is formed on a major surface of the solid electrolyte body 2 facing the reference gas chamber 12. The solid electrolyte body 2, the pump electrode 8p, and the reference electrode 8b form the pump cell 3. The solid electrolyte body 2, the monitor electrode 8m, and the reference electrode 8b form the monitor cell 4. The solid electrolyte body 2, the sensor electrode 8s, and reference electrode 8b form the sensor cell 5.

How to measure the concentration of NOx in the gas g will be described below. The gas g, as illustrated in FIG. 1, passes through the diffusion resistance layer 13 and then enters the gas chamber 7. The gas g contains oxygen molecules which are discharged using the pump cell 3. Specifically, a dc voltage is applied between the reference electrode 8b and the pump electrode 8p so as to place the reference electrode 8b at a higher potential. This causes the oxygen molecules to be reduced on the pump electrode 8p into oxygen ions which are then discharged into the reference gas chamber 12 through pumping action. The concentration of oxygen in the gas chamber 7 is controlled by regulating the degree of dc voltage applied to the pump cell 3.

The gas g whose concentration of oxygen has been decreased is delivered to the monitor cell 4 and the sensor cell 5. The gas g still contains the oxygen molecules which have not been removed by the pump cell 3. The concentration of such oxygen molecules is measured by the monitor cell 4. The dc voltage is, as illustrated in FIG. 3, applied between the reference electrode 8b and the monitor electrode 8m of the monitor cell 4 so as to place the reference electrode 8b at a higher potential. This will cause the oxygen molecules contained in the gas g to be reduced into oxygen ions which are then discharged into the reference gas chamber 12 through pumping action. The monitor electrode 8m is, as described later, made of a Pt—Au cermet electrode which is inactive to decomposition of NOx. The current (i.e., the monitor cell current Im) flowing through the monitor cell 4, thus, depends only on the concentration of oxygen molecules contained in the gas g, not the concentration of NOx.

The dc voltage is also applied between the reference electrode 8b and the sensor electrode 8s of the sensor cell 5 so as to place the reference electrode 8b at a higher potential. The sensor electrode 8s is, as described later, made of a Pt—Rh cermet electrode which is inactive to decomposition of NOx. The oxygen molecules and NOx molecules are, thus, reduced on the sensor electrode 8s into oxygen ions which are then discharged into the reference gas chamber 12 through the pumping action. The current (i.e., the sensor cell current Is) flowing through the sensor cell 5 is, therefore, depends on both the concentration of the oxygen molecules and the concentration of NOx molecules.

Figure 5:
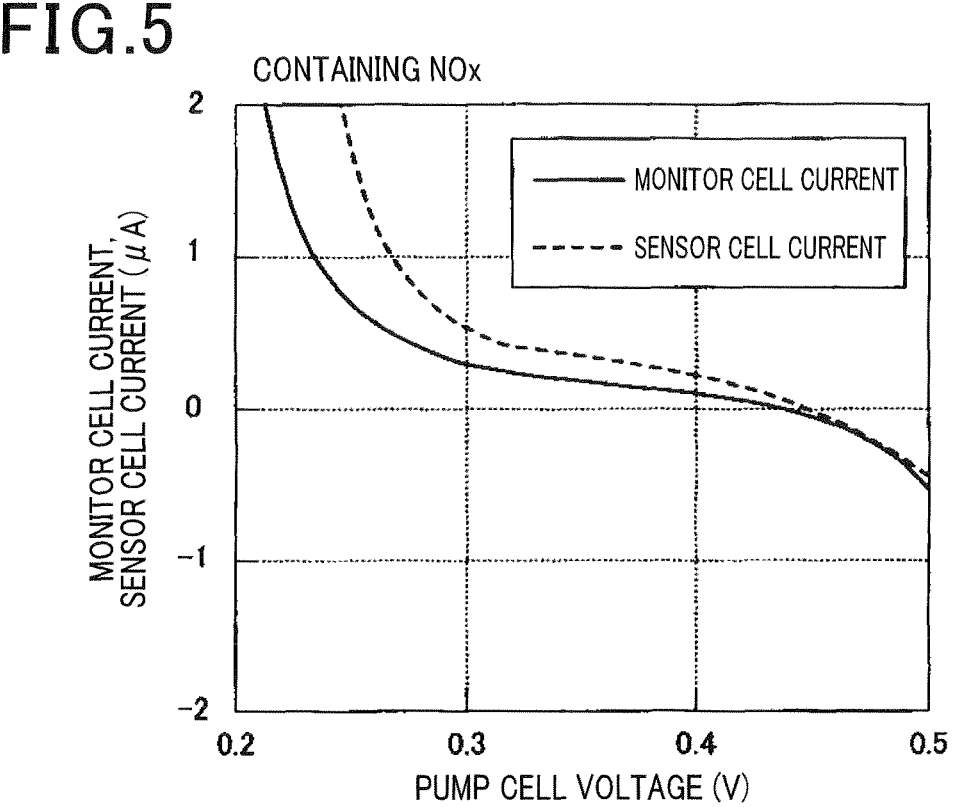
FIG. 5 is a graph which represents a relation among a pump cell voltage, a monitor cell current, and a sensor cell current when gas containing NOx is measured in the first embodiment.

When the voltage (i.e., the pump cell voltage Vp) applied to the pump cell 3 is, as illustrated in FIG. 5, decreased, it will cause the monitor cell current Im and the sensor cell current Is to increase. This is because a drop in the pump cell voltage Vp usually results in a decrease in amount of oxygen discharged from the gas g by the pump cell 3, so that the centration of oxygen in the gas g rises, thus causing the amount of oxygen pumped out by the monitor cell 4 and the sensor cell 5 to increase the amount of oxygen ion flowing through the monitor cell 4 and the sensor cell 5, which will lead to increases in the monitor cell current Im and the sensor cell current Is.

For measurement of the concentration of NOx, the pump cell voltage Vp is set to a given level, e.g., about 0.37V.

Figure 6:
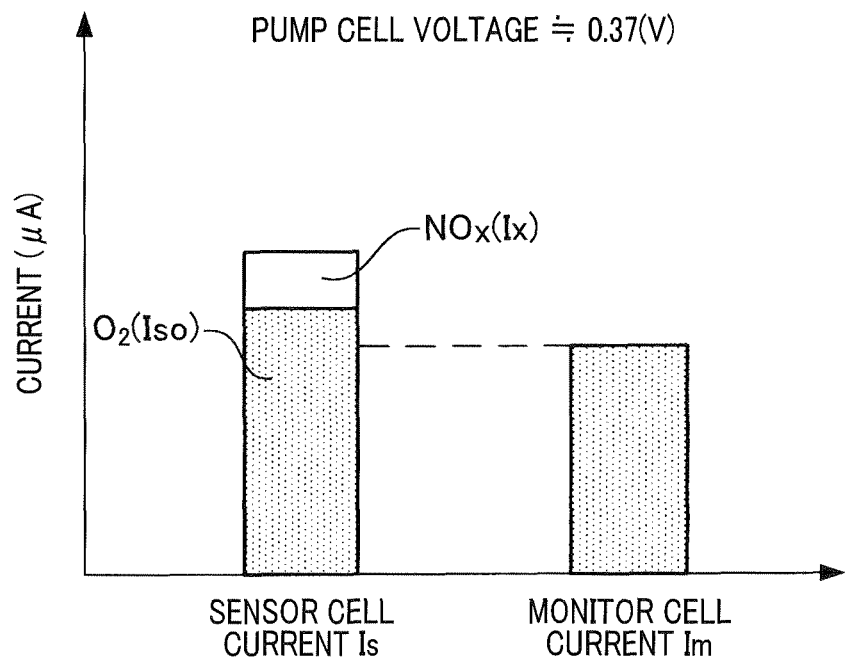
FIG. 6 is a graph which represents breakdowns of a sensor cell current and a monitor cell current when Vp is set to about 0.37V in FIG. 5.

The sensor cell 5 is, as described above, active to both the given gas component and oxygen, so that the sensor cell current Is, as can be seen from FIG. 6, includes the given gas dependent current Ix arising from the concentration of the given gas component and the oxygen dependent current Iso arising from the concentration of oxygen. The monitor cell 4 is active only to oxygen, so that the monitor cell current Im does not have a component developed by the concentration of the given gas component.

The monitor cell current Im is, as can been seen in FIG. 6, slightly lower than the oxygen dependent current Iso. In other words, the monitor cell 4 and the sensor cell 5 are different in sensitivity to the concentration of oxygen from each other. This is because the electrodes 8 of the monitor cell 4 and the sensor cell 5 are different in material from each other, and there is a production variability in size of areas between them. This will lead to an error in subtracting the monitor cell current Im from the sensor cell current Is to derive the given gas dependent current Ix in calculating the concentration of the given gas component.

Accordingly, in this embodiment, the correction operation is performed to bring the monitor cell current Im close to the oxygen dependent current Iso. Specifically, the calculating portion 11 (see FIG. 1) stores therein a value derived by dividing the oxygen dependent current Iso by the monitor cell current Im as a sensitivity ratio a and substituting the sensor cell current Is, the monitor cell current Im which have been measured, and the sensitivity ratio a into an equation below to derive the given gas dependent current Ix.

$$Is - aIm = Ix$$

The given gas dependent current Ix, as calculated above, is used to determine the concentration of the given gas component. Note that since $Is - aIm = (Ix + Iso) - Iso/Im \times Im = Ix$, $Is - aIm$ is equal to Ix.

Because of a unit-to-unit variability of the gas sensor 10, the sensitivity ratio a needs to be measured and stored. For instance, when the gas concentration measuring apparatus 1 is produced and shipped, the atmospheric air which does not contain the given gas component is measured as the gas g. Using resulting values of the sensor cell current Is and the monitor cell current Im, the sensitivity ratio a is calculated.

When the gas g contains the given gas component, it is impossible to directly measure the oxygen dependent current Iso, however, when the gas g does not contain the given gas component, a relation of the sensor cell current Is=the oxygen dependent current Iso will be met, thus making it possible to directly measure the oxygen dependent current Iso. The sensitivity ratio a is, therefore, derived using the following equation.

$$a=Iso/Im=Is/Im$$

Figure 7:
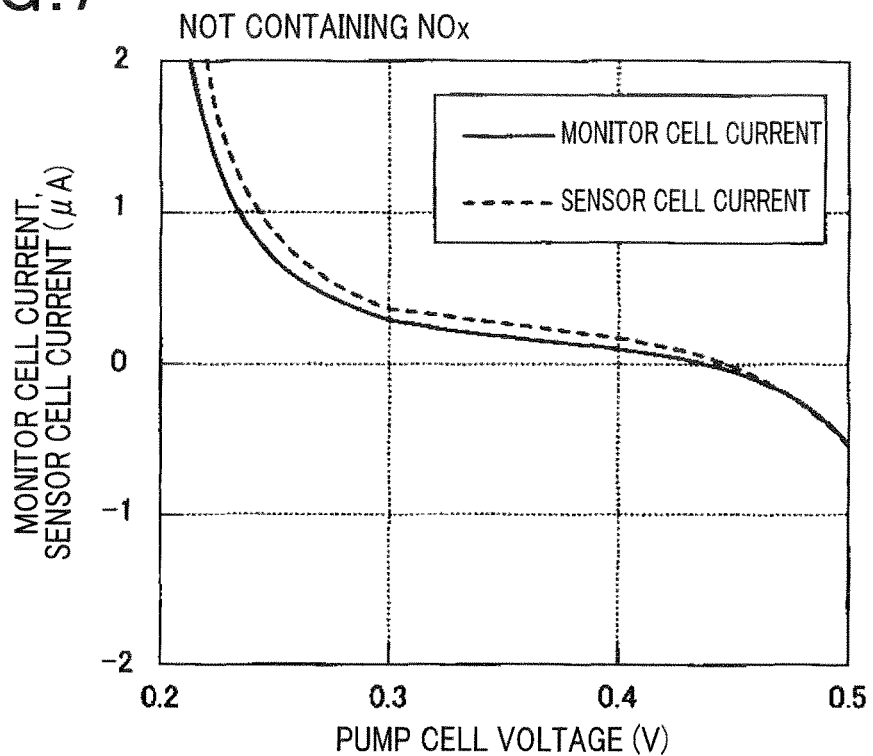
FIG. 7 is a graph which represents a relation among a pump cell voltage, a monitor cell current, and a sensor cell current when gas not containing NOx is measured in the first embodiment.

The graph of FIG. 7 shows that when the atmospheric air which does not contain the given gas component is measured, it will cause the sensor cell current Is to be slightly higher than the monitor cell current Im. This is because the sensor cell 5 is higher in sensitivity to oxygen than the monitor cell 4. The sensitivity ratio a(=Is/Im) is often higher than one.

Figure 8:
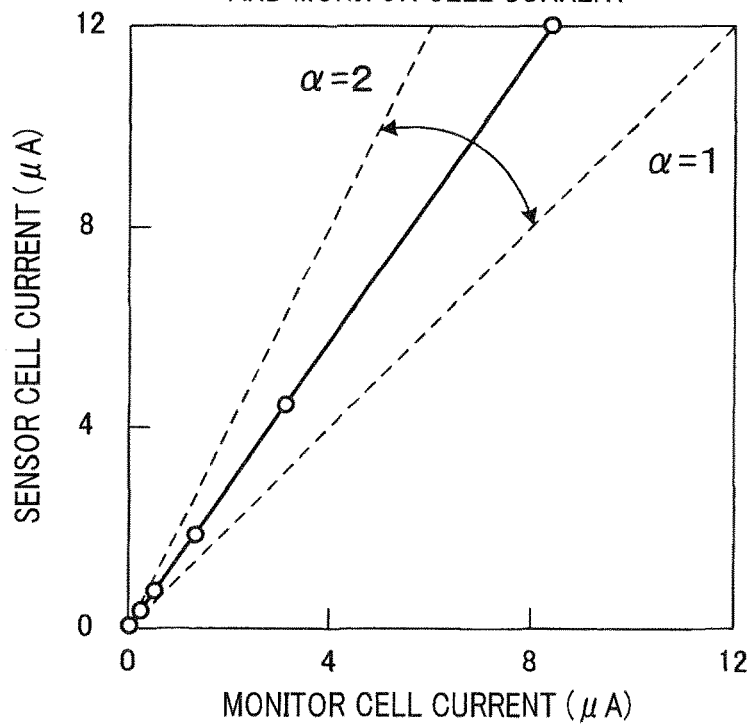
FIG. 8 is a graph which represents a correlation between a monitor cell current and a sensor cell current when gas not containing NOx is measured in the first embodiment.

In this embodiment, in a condition where the gas g does not contain the given gas component, the pump cell voltage Vp is changed stepwise to make conditions within the gas chamber 7 which are different in value of the concentration of oxygen. In each of the conditions, the monitor cell current Im and the sensor cell current Is are measured. FIG. 8 represents a correlation between the monitor cell current Im and the sensor cell current Is, as derived in the above way.

When the pump cell voltage Vp is lower, the concentration of oxygen in the gas g (i.e., the atmospheric air) increases, so that the monitor cell current Im and the sensor cell current Is increase. Conversely, when the pump cell voltage Vp is higher, the concentration of oxygen in the gas g decreases, so that the monitor cell current Im and the sensor cell current Is decreases. FIG. 8 shows that values of the monitor cell current Im and the sensor cell current Is, as measured when the concentration of oxygen in the gas g is changed, appear on a straight line. In this embodiment, the slope of such a straight line is used as the sensitivity ratio a(=Is/Im). The determination of the slope of the straight line is achieved using the least-square technique.

The sensitivity ratio a, as described above, depends upon the individual variability of the gas sensor 10. The sensitivity ratio a, that is, the slope of the straight line in FIG. 8 has a value of 1 to 2 in most gas sensors 10.

Figure 9:
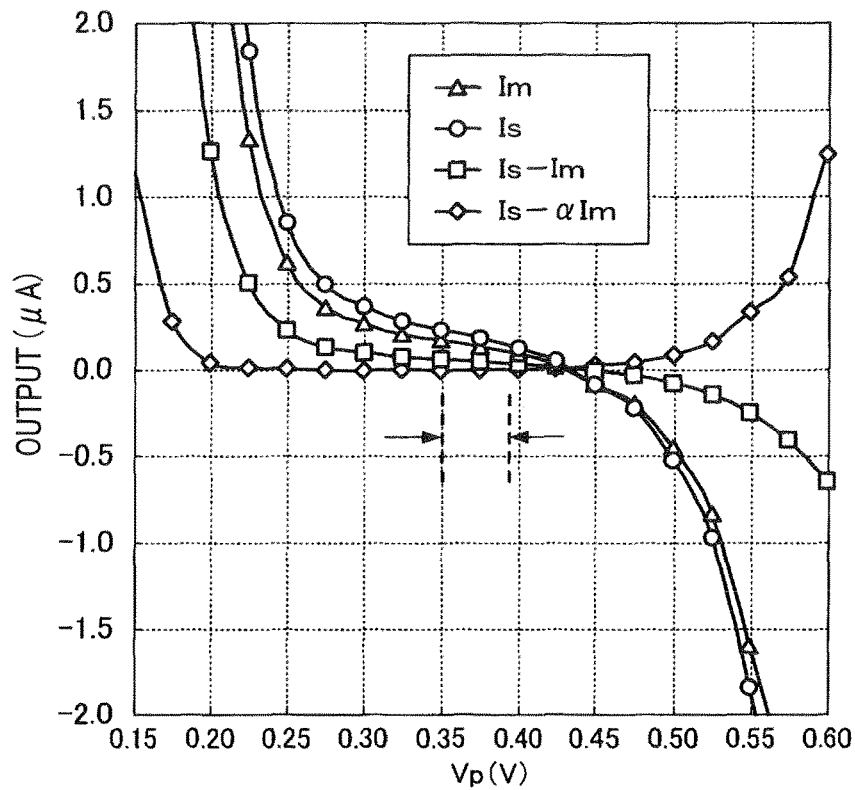
FIG. 9 is a graph which represents a relation among a pump cell voltage Vp, Im, Is, Im−Is, and Im−αIs when gas not containing NOx is measured in the first embodiment.

The graph of FIG. 9 represents a relation among the pump cell voltage Vp, Im, Is, Is−Im, and Is−aIm when the gas g which does not contain NOx is measured. The graph shows that a value derived by subtracting the monitor cell current Im from the sensor cell current Is (i.e., Is−Im) will be a great value equivalent to about ±6 ppm, as converted in terms of concentration of NOx, in a range of 0.35 to 0.39V of the pump cell voltage Vp (i.e., a range where the pump cell voltage Vp will vary when the concentration of NOx is measured). In contrast, a value derived by multiplying the monitor cell current Im by the sensitivity ratio a in the correction operation and subtracting it from the sensor cell current Is (i.e., Is−aIm) will be a small value equivalent to ±1 ppm or less, as converted in terms of concentration of NOx which is lower than Is−Im in a range of 0.35 to 0.39V of the pump cell voltage Vp.

When the gas g containing NOx is measured, the sensor cell current Is, as illustrated in FIG. 6, will be the sum of the given gas dependent current Ix and the oxygen dependent current Iso. In this embodiment, the Iso and aIm are adjusted to be substantially equal to each other, so that the concentration of NOx, as derived from Iso−aIm, will be ±1 ppm or less, thus resulting in enhanced accuracy in calculating the given gas dependent current Ix.

The characteristics of the electrode 8 of the gas sensor 10 changes with time, so that the sensitivity ratio a will change with time. It is, thus, necessary to measure the sensitivity ratio a at regular intervals to update and store the value of the sensitivity ratio a.

Before the gas concentration measuring apparatus 1 is installed in the automotive vehicle, it is, as described above, possible to measure the gas g which does not contain the given gas component, so that a relation of Is=Iso is met. A relation of a=Iso/Im=Is/Im is, thus, derived, which enables the sensitivity ratio a to be calculated accurately.

However, after the gas concentration measuring apparatus 1 is mounted in the automotive vehicle, it is impossible to measure the atmospheric air which does not contain the given gas component (i.e., NOx). When the gas g contains the given gas component, it is impossible to directly measure the oxygen dependent current Iso, thus resulting in an error in measuring the sensitivity ratio a(=Iso/Im).

Figure 10:
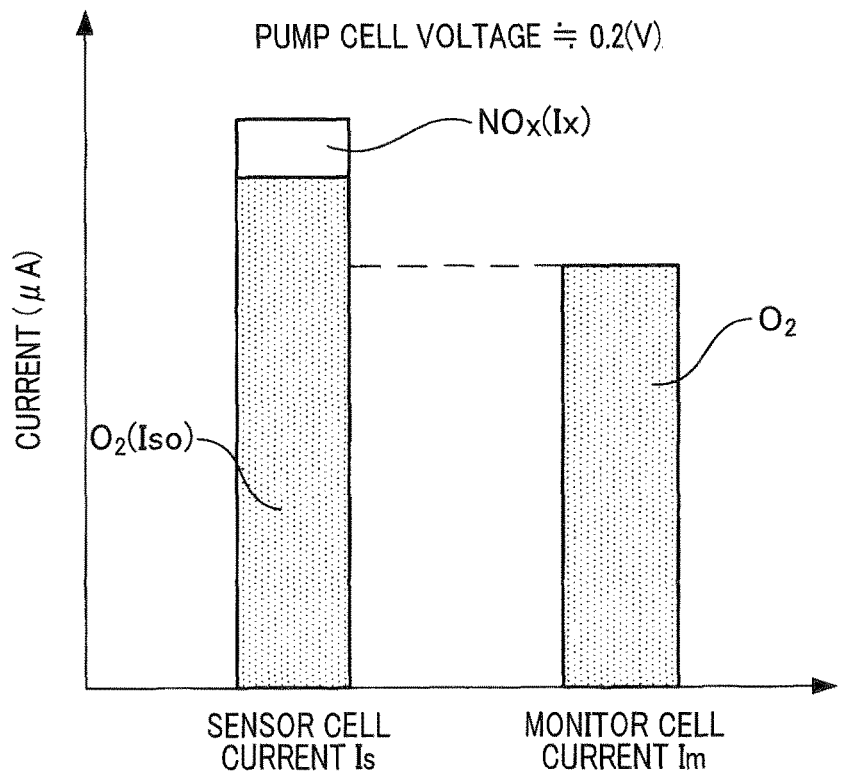
FIG. 10 is a graph which represents breakdowns of a sensor cell current and a monitor cell current when gas containing NOx is measured at Vp set to about 0.2V in the first embodiment.
Figure 11:
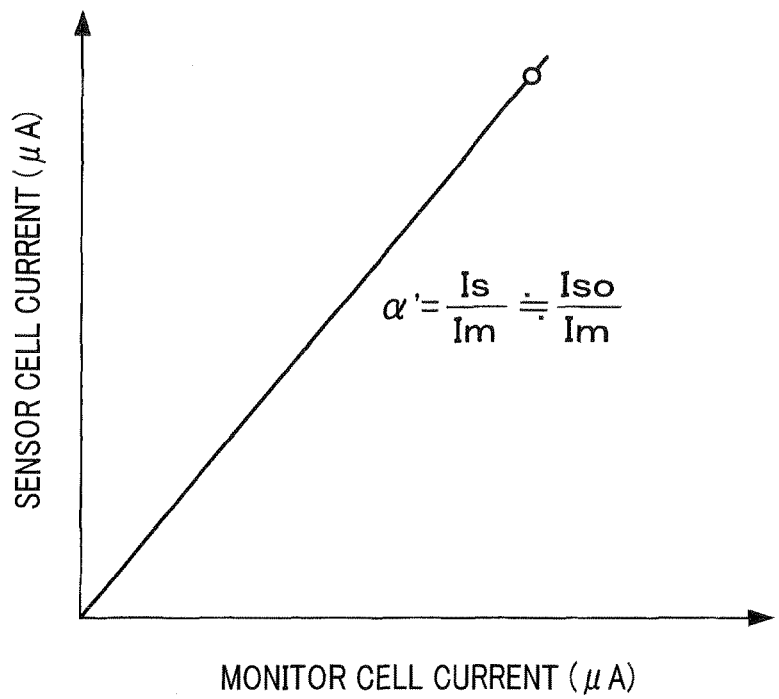
FIG. 11 is a correlation between the monitor cell current and the sensor cell current in FIG. 10.

Consequently, in this embodiment, an approximate value a' of the sensitivity ratio a is calculated at regular intervals. Specifically, when the concentration of NOx is measured, the pump cell voltage Vp is, as described above, set to approximately 0.37V, while when the approximate value a' of the sensitivity ratio a is calculated, the pump cell voltage Vp is set to a value lower than 0.37V, for example, approximately 0.2V. This results in a decrease in amount of oxygen molecules discharged by the pump cell 3, so that the concentration of oxygen in the gas g will increase which is greatly higher than the concentration of the given gas component, so that a percentage of the oxygen dependent current Iso in the sensor cell current Is, as indicated in FIG. 10, will be much higher than that of the given gas dependent current Ix. It is, thus, possible to ignore the given gas dependent current Ix, thereby enabling, as illustrated in FIG. 11, the approximate value a'(=Is/Im) to be derived as being substantially equal to the sensitivity ratio a(=Iso/Im).

After the approximate value a' is calculated, an equation below is used to determine the concentration of the given gas component. Specifically, measured values of the sensor cell current Is, the monitor cell current Im, and the approximate value a' are substituted into the equation below to determine an approximate value Ix' of the given gas dependent current Ix. Use of the approximate value Ix' enables the concentration of the given gas component to be calculated with high accuracy.

$$Is-a'Im=Ix'$$

The structure of the gas sensor 10 will be described below in detail. The gas sensor 10 is, as illustrated in FIGS. 1 to 4, equipped with the single solid electrolyte body 2. The pump electrode 8p, the monitor electrode 8m, the sensor electrode 8s, and the reference electrode 8b are formed in or on the solid electrolyte body 2. Specifically, in this embodiment, the single solid electrolyte body 2 is used to make three cells: the pump cell 3, the monitor cell 4, and the sensor cell 5.

Figure 4:
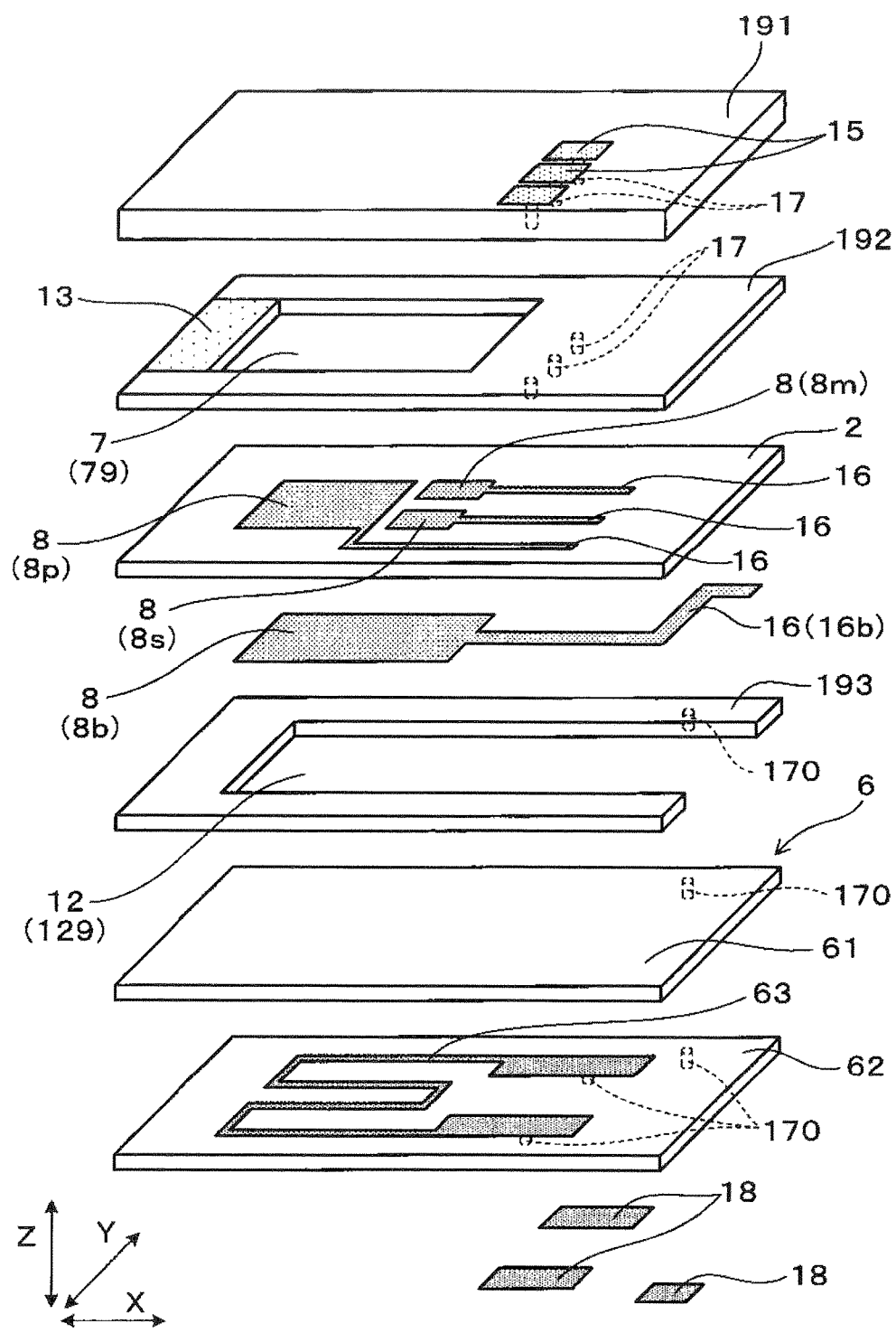
FIG. 4 is an exploded perspective view of a gas sensor in the first embodiment.

The gas sensor 10, as illustrated in FIGS. 1 and 4, includes an insulating plate 191 made of ceramic, a first spacer 192 which is sheet-like and defines the gas chamber 7, the solid electrolyte body 2, a second spacer 193 which is sheet-like and defines the reference gas chamber 12, and a heater 6 which are all stacked in a width-wise direction of the heater 6 (i.e., z-direction).

The first spacer 192, as illustrated in FIG. 4, has formed therein a first cut-out 79 which defines the gas chamber 7.

The first spacer 192 also has the diffusion resistance layer 13 through which the gas g is admitted from the exhaust pipe to the gas chamber 7. The diffusion resistance layer 13 works to limit the rate at which the gas g flows.

The second spacer 193 has a second cut-out 129 formed therein. The second cut-out 129 defines the reference gas chamber 12. The second cut-out 129 communicates with an external space in which atmospheric air exists. The first spacer 192 and the second spacer 193 are made of insulating material such as alumina.

The pump electrode 8p and the monitor electrode 8m are made of metallic material which is low in activity to decompose NOx. Specifically, the electrodes 8p and 8m are made of a porous cermet electrode which mainly contains gold Au and platinum Pt. A content of Au in the electrodes 8p and 8m is 1 to 10 by weight percent. The sensor electrode 8s is made of metallic material which is high in activity to decompose NOx. Specifically, the sensor electrode 8s is made of a porous cermet electrode which mainly contains Platinum Pt and rhodium Rh.

The electrodes 8 have formed thereon leads 16 which define current paths. The solid electrolyte body 2, the first spacer 192, and the insulating plate 191 have formed therein through-holes 17 passing therethrough in the z-direction. Metallic plugs are formed in the through holes 17. The insulating plate 191 has formed on a surface thereof a plurality of pads 15 for electrical connections with an external device. Each of the pads 15 electrically connects with one of the electrodes 8m, 8s, and 8p through the plug 16.

The heater 6 is made up of a ceramic heater sheet 62, a heater electrode 63 which is formed on the surface of the heater sheet 62 and works to produce heat when electrically energized, and an insulating layer 61 which covers the heater electrode 63. The heater 6 is designed to have the heater electrode 63 which produces heat when supplied with electricity from an external device to heat the above described cells 3, 4, and 5 up to an activation temperature thereof. The second spacer 193, the insulating layer 61, and the heater sheet 62 have through-holes 170 formed therein. The heater sheet 62 has pads 18 formed on the surface thereof. Metallic plugs are formed in the through-holes 170 to establish electrical connections of the heater electrode 63 and the reference electrode 8b with the pads 18.

The center where the heater electrode 63 produces heat is located closer to the pump cell 3. In other words, the cells 3, 4, and 5 are heated using the heater electrode 63 so that the temperature of the pump cell 3 becomes higher than those of the monitor cell 4 and the sensor cell 5.

The gas chamber 7 of this embodiment is, as illustrated in FIGS. 1 and 2, integrally formed to have a space which is entirely constant both in the z-direction and in a width-wise direction (i.e., the y-direction) perpendicular to both the x- and z-directions from where the pump cell 3 is formed to where the monitor cell 4 and the sensor cell 5 are formed. In other words, there is not an object, such as an orifice or a partition, which decreases the space in the z-direction or the y-direction from where the pump cell 3 is formed to where the monitor cell 4 and the sensor cell 5 are formed in the gas chamber 7, thereby causing the gas g to flow without being subjected to diffusion limitation from where the pump cell 3 is formed to where the monitor cell 4 and the sensor cell 5 are formed.

The distance L1, as illustrated in FIG. 2, between the pump electrode 8p and the monitor electrode 8m and the distance L2 between the pump electrode 8p and the sensor electrode 8s are equal to each other in the x-direction.

The reference electrode 8b is, as can be seen in FIGS. 1 and 4, a common electrode. In other words, portions of the reference electrode 8b which constitute the pump cell 3, the monitor cell 4, and the sensor cell 5 are integrally formed.

The operations and beneficial effects of this embodiment will be described. The calculating portion 11 of the gas concentration measuring apparatus 1 works to correct the monitor cell current Im to bring it close to the oxygen dependent current Iso when determining the concentration of the given gas component. This enhances the accuracy in calculating the concentration of the given gas component. Specifically, the sensor cell current Is, as described above, includes the given gas dependent current Ix that is a component arising from the concentration of the given gas component and the oxygen dependent current Iso. The above correction operation is, therefore, made to approximate the monitor cell current Im' after corrected to the oxygen dependent current Iso. Subtraction of the monitor cell current Im' from the sensor cell current Is(=Ix+Iso), thus, derives a relation of Is−Im'=(Ix+Iso)−Im'≈Ix, which enables the given gas dependent current Ix to be calculated accurately. This results in an enhanced accuracy in determining the concentration of the given gas component.

The calculating portion 11 also uses the following equation to calculate the given gas dependent current Ix in the sensor cell current Is.

$$Is-aIm=Ix$$

The given gas dependent current Ix, as derived above, is used to determine the concentration of the given gas component. This facilitates and ensures the calculation of the given gas dependent current Ix in the sensor cell current Is.

In this embodiment, the sensor cell current Is and the monitor cell current Im are, as illustrated in FIGS. 7 and 8, measured in the condition where the gas g does not contain the given gas component. In such a condition, since the sensor cell current Is does not contain the given gas dependent current Ix, a relation of the sensor cell current Is=the oxygen dependent current Iso is met. It is, therefore, possible to use the following equation to calculate the sensitivity ratio a easily and accurately.

$$a=Iso/Im=Is/Im$$

In this embodiment, the calculation of the sensitivity ratio a is achieved, as illustrated in FIGS. 7 and 8, by changing the pump cell voltage Vp. This makes a plurality of conditions which have different values of the concentration of oxygen in the gas g within the gas chamber 7. In each condition, the sensor cell current Is and the monitor cell current Im are measured to derive the sensitivity ratio a.

The use of the plurality of measured data enables the sensitivity ratio a to be determined more accurately.

In this embodiment, after the gas sensor 10 is installed in the automotive vehicle, the gas g containing the given gas component is used to calculate the approximate value a' of the sensitivity ratio a. This calculation is achieved by setting the pump cell voltage Vp to be lower than that when the concentration of the given gas component is determined. The approximate value a' is derived using the following equation.

$$Is/Im=a'$$

It makes it possible to use the gas g containing the given gas component to calculate the approximate value a' that approximates the sensitivity ratio a. The sensitivity ratio a, as already described, changes with time, thus requiring the need for updating the sensitivity ratio a cyclically. Once the gas concentration measuring apparatus is mounted in the automotive vehicle, it is impossible to measure the atmospheric air as the gas g which does not contain the given gas component (NOx). In this embodiment, it is possible to derive the value approximating the sensitivity ratio a even when the gas g contains the given gas component, thus ensuring the accuracy in measuring the concentration of the given gas component even if the sensitivity ratio a changes with time.

It is preferable that the calculation of the approximate value a' is made when the concentration of the given gas component is as low as possible, like when the engine of the vehicle is undergoing a fuel cut.

The gas sensor 10 of this embodiment, as illustrated in FIGS. 1 and 2, is formed integrally so as to have a width which is entirely constant in the z-direction from where the pump cell 2 is formed to where the monitor cell 4 and the sensor cell 5 are formed. In other words, the is not an object, such as an orifice or a partition, which decreases the space in the z-direction or the y-direction from where the pump cell 3 is formed to where the monitor cell 4 and the sensor cell 5 are formed within the gas chamber 7, thereby causing the gas g to flow without being subjected to diffusion limitation from where the pump cell 3 is formed to where the monitor cell 4 and the sensor cell 5 are formed. This achieves quick detection of a change in concentration of the given gas component, thus enhancing the response rate of the gas sensor 10.

In this embodiment, the single solid electrolyte body 2 is, as illustrated in FIGS. 1 to 4, shared among the pump cell 3, the monitor cell 4, and the sensor cell 5. This eliminates the need for using a plurality of solid electrolyte bodies, thus resulting in a decrease in production cost of the gas sensor 10.

It is, thus, possible to provide a gas concentration measuring apparatus which is capable of measuring the concentration of the given gas component more accurately.

Second Embodiment

In the following embodiments, the same reference symbols used in the drawings as those in the first embodiment will refer to the same parts unless otherwise specified.

Figure 12:
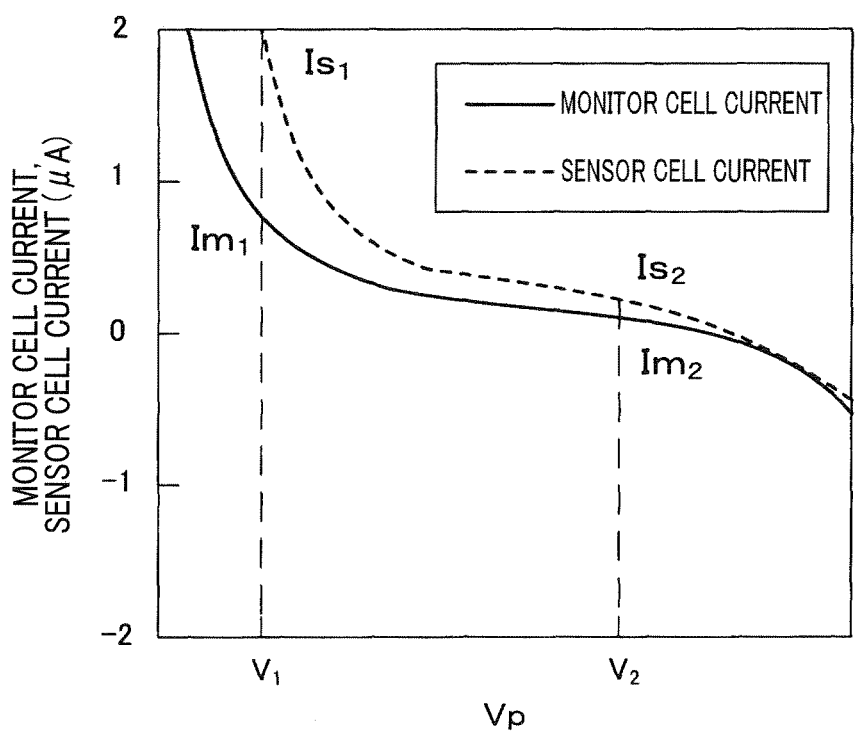
FIG. 12 is a graph which represents a relation among a pump cell voltage, a monitor cell current, and a sensor cell current in terms of V1, V2, $Im_1$, $Im_2$, $Is_1$, and $Is_2$ when gas containing NOx is measured.

This embodiment is an example of a modification of how to calculate the approximate value a' of the sensitivity ratio a using the gas g containing the given gas component. A first voltage V1 and a second voltage V2 which are different in level from each other are, as illustrated in FIG. 12, applied to the pump cell 3. The monitor cell current $Im_1$ and the sensor cell current $Is_1$ when the first voltage V1 is applied are measured. The monitor cell current $Im_2$ and the sensor cell current $Is_2$ when the second voltage V2 is applied are measured. The measured values $Im_1$, $Is_1$, $Im_2$, and $Is_2$ are used to determine the approximate value a' according to an equation below.

$$(Is_1 - Is_2)/(Im_1 - Im_2) = a' \quad (1)$$

Figure 13:
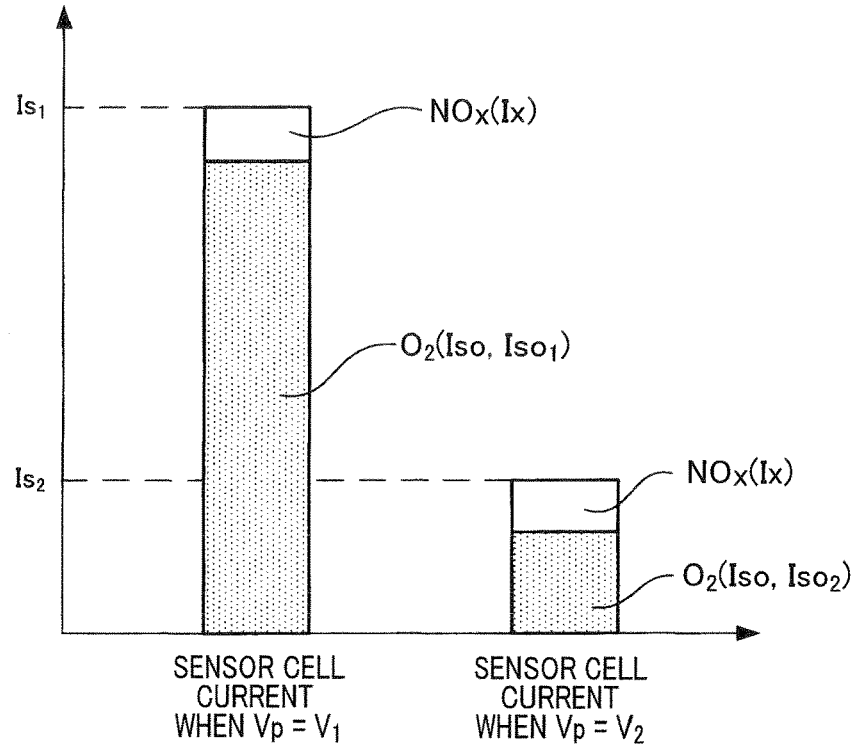
FIG. 13 is a graph which represents a breakdown of a sensor cell current when a pump cell voltage Vp is set to V1 or V2 in FIG. 12.

The sensor cell current $Is_1$ and $Is_2$, as can be seen from FIG. 13, each include the given gas dependent current Ix that is a component arising from the concentration of the given gas component and the oxygen dependent current Iso that is a component arising from the concentration of oxygen. The sensor cell current $Is_1$ and $Is_2$ are values measured by changing the pump cell voltage Vp, so that values of the oxygen dependent current Iso are different from each other. Specifically, when the pump cell voltage Vp is low (i.e., the first voltage V1), the concentration of oxygen in the gas g will be high, so that the value of the oxygen dependent current Iso will be high. Alternatively, when the pump cell voltage Vp is high (i.e., the second voltage V2), the concentration of oxygen in the gas g will be low, so that the value of the oxygen dependent current Iso will be low.

In contrast, the concentration of the given gas component is not affected by the pump cell voltage Vp, so that the given gas dependent current Ix does not change between when Vp=V1 and when Vp=V2. The elimination of the given gas dependent current Ix is, therefore, achieved by deriving $Is_1 - Is_2$ in the above equation (1). The oxygen dependent current Iso ($Iso_2$) when Vp=V2 will be much lower than the oxygen dependent current Iso ($Iso_1$) when Vp=V1.

Figure 14:
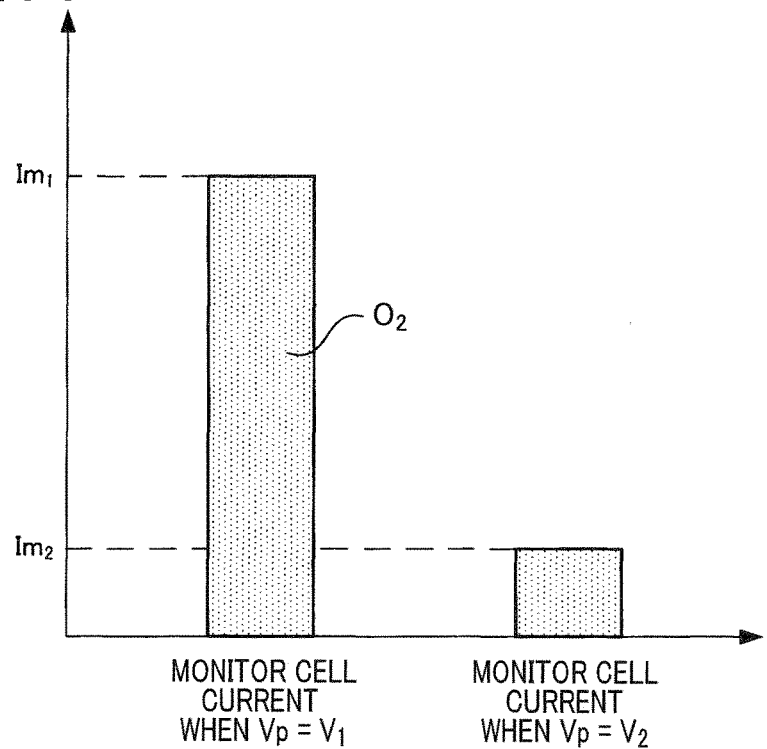
FIG. 14 is a graph which represents a breakdown of a monitor cell current when a pump cell voltage Vp is set to V1 or V2 in FIG. 12.

Similarly, as illustrated in FIG. 14, when the pump cell voltage Vp is low (i.e., the first voltage V1), the monitor cell current $Im_1$ will be high. Alternatively, when the pump cell voltage Vp is high (i.e., the second voltage V2), the monitor cell current $Im_2$ will be low.

As described above, use of the above equation (1) eliminates the given gas dependent current Ix, so that the approximate value a' is not affected by the concentration of the given gas component, thus enabling the approximate value a' which is very close to the sensitivity ratio a to be derived.

After the approximate value a' is calculated, the concentration of the given gas component is, like in the first embodiment, determined accurately using an equation below.

$$Is - a'Im = Ix'$$

This embodiment offers the same arrangements and beneficial effects as those in the first embodiment.

Third Embodiment

Figure 15:
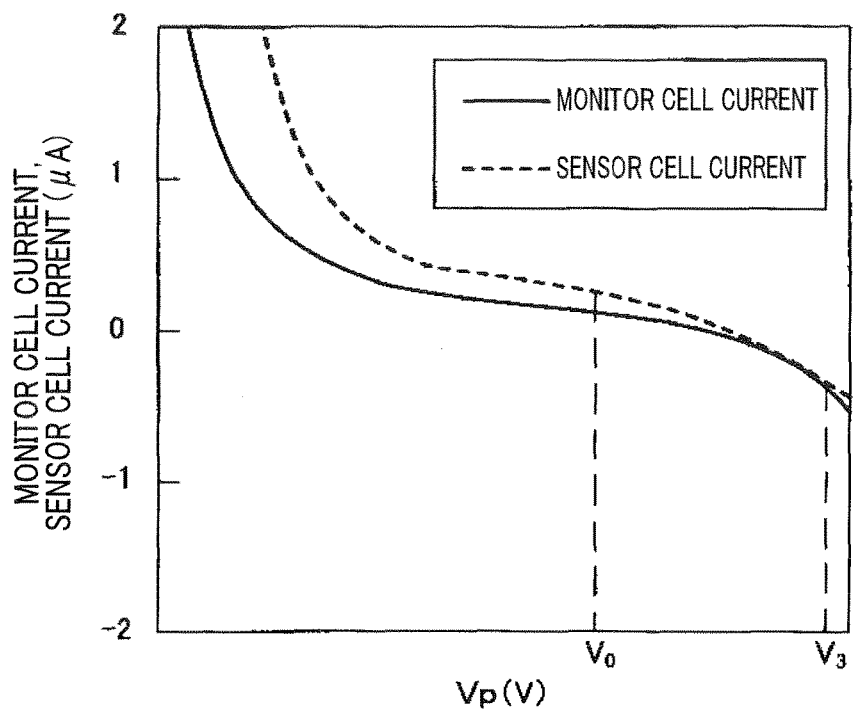
FIG. 15 is a graph which represents a relation among a pump cell voltage, a monitor cell current, and a sensor cell current in terms of values of V0 and V3 when gas containing NOx is measured in the third embodiment.
Figure 16:
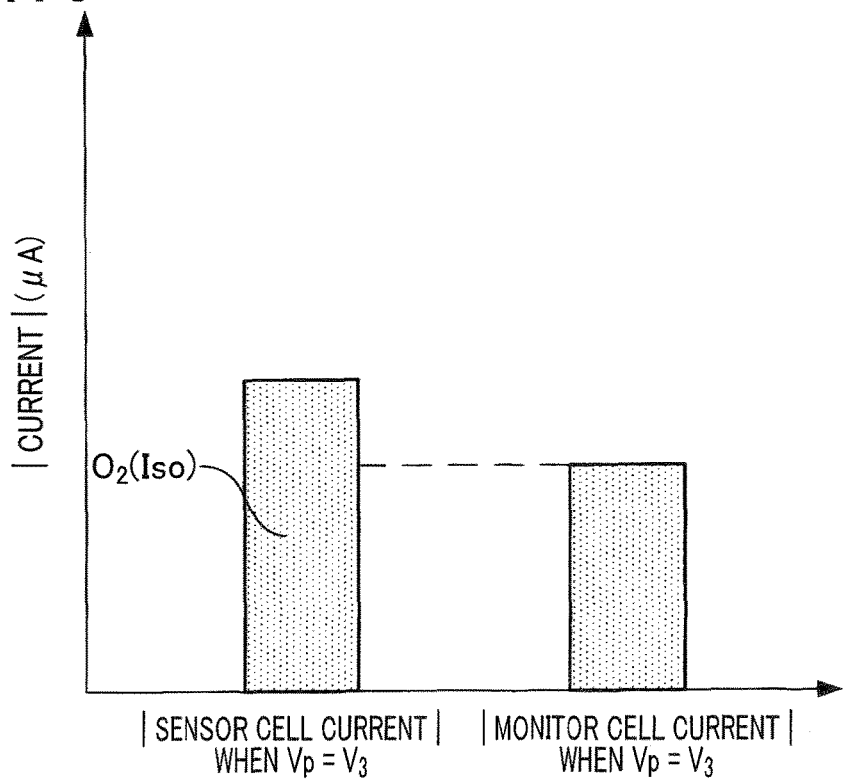
FIG. 16 is a graph which represents breakdowns of |a sensor cell current| and |a monitor cell current| when a pump cell voltage Vp is set to V3, as illustrated in FIG. 15.

This embodiment is an example of a modification of how to calculate the approximate value a' of the sensitivity ratio a using the gas g containing the given gas component. In this embodiment, the pump cell voltage Vp for use in calculating the approximate value a' is, as illustrated in FIG. 15, set to a level V3 which is higher than a level V0 used to calculate the concentration of the given gas component. This causes the NOx that is the given gas component to be decomposed on the pump electrode 8p (see FIGS. 1 and 2). The monitor cell current Im and the sensor cell current Is are then measured. Since the given gas component in the gas g will be decomposed, the sensor cell current Is, as illustrated in FIG. 16, does not include the given gas dependent current Ix, but contains only the oxygen dependent current Iso. This enables the approximate value a' of the sensitivity ratio a to be calculated according to an equation below.

$$a' = Iso/Im = Is/Im$$

Too high a level of the pump cell voltage Vp will cause $H_2O$ contained in the gas g to be decomposed on the pump electrode 8p, so that $H_2$ gas is generated. The $H_2$ gas then flows on the monitor cell 4 and the sensor cell 5, thereby causing the monitor cell current Im and the sensor cell current Is to have minus values. When such values are used to calculate the sensitivity ratio, it will cause the sensitivity to $H_2$ to be derived. Consequently, the determination of the sensitivity ratio a to $O_2$ requires use of plus values of the monitor cell current Im and the sensor cell current Is.

This embodiment offers the same arrangements and beneficial effects as those in the first embodiment.

Fourth Embodiment

This embodiment is an example of a modification of how to calculate the given gas dependent current Ix. It is known that an offset current $I_{off}$ usually flows through the monitor cell 4 and the sensor cell 5 regardless of presence of oxygen and the given gas component. The offset current $I_{off}$ is thought of as arising from electron conduction occurring between the solid electrolyte body 2 and the electrode 8. In this embodiment, the monitor cell current Im is corrected under the assumption that the monitor cell current Im and the sensor cell current Is contain the offset current $I_{off}$. This will be described below in detail.

Figure 17:
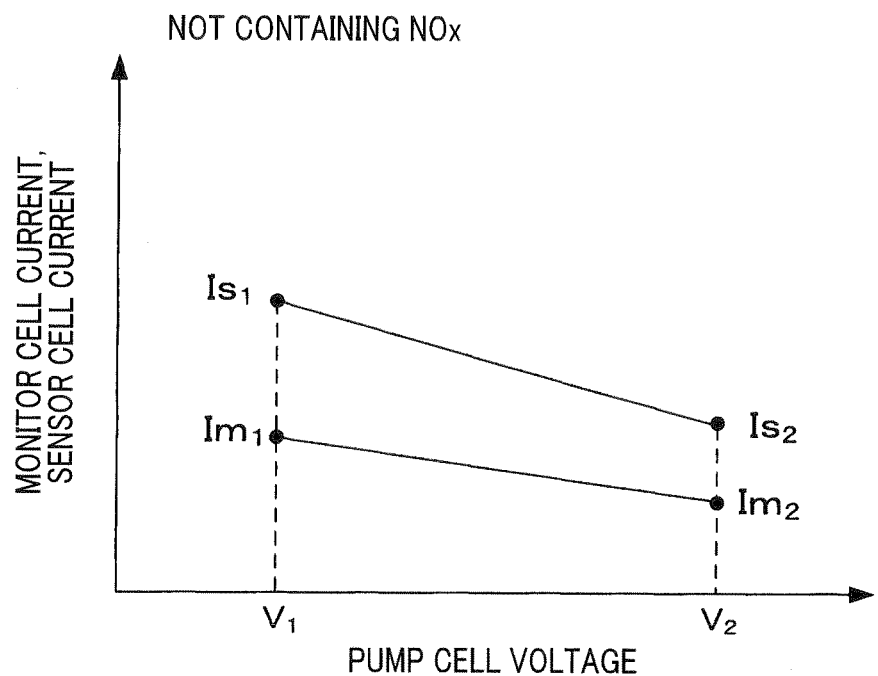
FIG. 17 is a graph which represents a relation among a pump cell voltage, a monitor cell current, and a sensor cell current in terms of values of V1 and V2 when gas not containing NOx is measured in the fourth embodiment.

In this embodiment, when the gas concentration measuring apparatus 1 is shipped, the atmospheric air not containing NOx is used to measure the sensor cell current Is and the monitor cell current Im. Specifically, a first voltage V1 and a second voltage V2 which are different in level from each other are applied to the pump cell 3 (see FIG. 17). The sensor cell current $Is_1$ and the monitor cell current $Im_1$ when the first voltage V1 is applied are measured. The sensor cell current $Is_2$ and the monitor cell current $Im_2$ when the second voltage V2 is applied are measured.

When the first voltage V1 which is lower than the second voltage V2 is applied to the pump cell 3, the concentration of $O_2$ within the gas chamber 7 will be higher than that when the second voltage V2 which is higher than the first voltage V1 is applied to the pump cell 3. Therefore, values of the sensor cell current $Is_1$ and the monitor cell current $Im_1$ when the first voltage V1 is applied will be greater than those of the sensor cell current $Is_2$ and the monitor cell current $Im_2$ when the second voltage V2 is applied.

Figure 18:
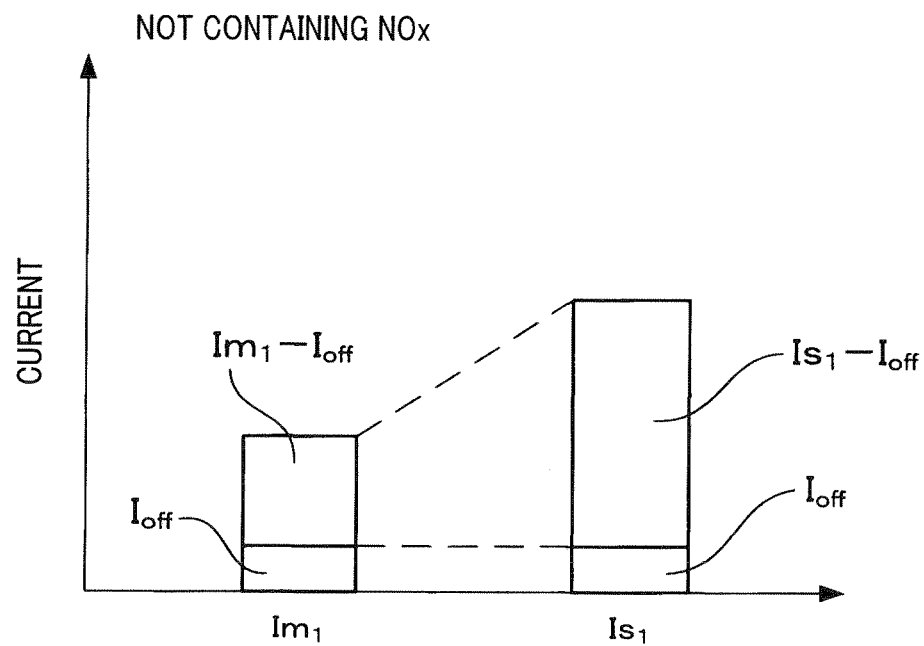
FIG. 18 is a graph which shows breakdowns of $Im_1$ and $Is_1$ in the fourth embodiment.
Figure 19:
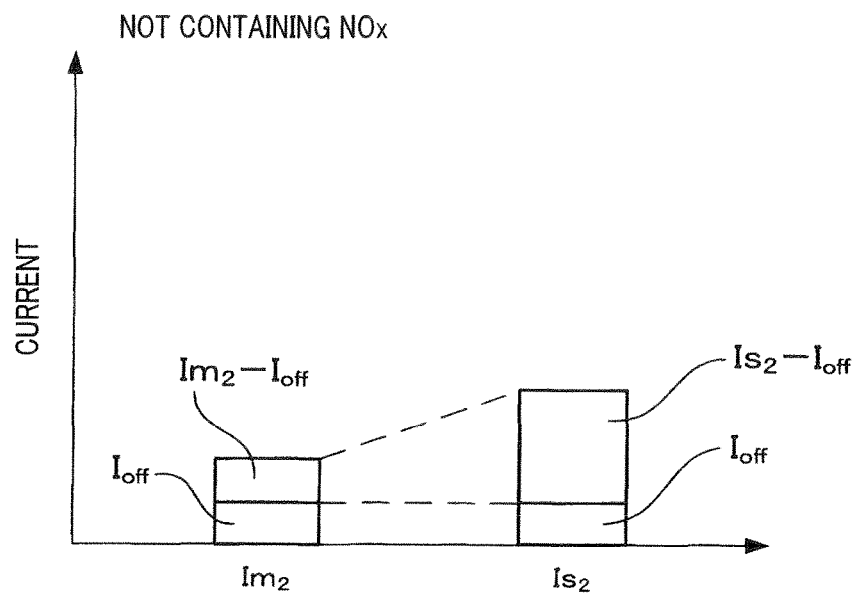
FIG. 19 is a graph which shows breakdowns of $Im_2$ and $Is_2$ in the fourth embodiment.

The monitor cell currents $Im_1$ and $Im_2$ (see FIG. 19) and the sensor cell current $Is_1$ and $Is_2$, as illustrated in FIGS. 18 and 19, each contain the offset current $I_{off}$. The offset current $I_{off}$ does not depend upon the concentration of oxygen, so that values of the offset currents $I_{off}$ contained in the currents $Im_1$, $Im_2$, $Is_1$, and $Is_2$ are substantially identical with each other.

Components of the monitor cell current $Im_1$ and the sensor cell current $Is_1$ which are sensitive to the concentration of oxygen are only components $(Im_1-I_{off})$ and $(Is_1-I_{off})$ thereof from which the offset current $I_{off}$ is removed. A ratio of $Im_1-I_{off}$ to $Is_1-I_{off}$ is defined as a subtracted value sensitivity ratio β.

$$\beta=(Is_1-I_{off})/(Im_1-I_{off})$$

The subtracted value sensitivity ratio β is constant even when the pump cell voltage Vp is changed to change the concentration of oxygen in the gas chamber 7 (see FIG. 19). The subtracted value sensitivity ratio β when the pump cell voltage Vp is set to the above second voltage V2 is given by $$\beta=(Is_2-I_{off})/(Im_2-I_{off})$$

Therefore, the subtracted value sensitivity ratio β is generally defined by the following formula.

$$\beta=(Is-I_{off})/(Im-I_{off})$$

It is apparent from FIGS. 18 and 19 that the sensor cell current $Is_1$ and $Is_2$ are expressed by $$Is_1=\beta(Im_1-I_{off})+I_{off}$$

$$Is_2=\beta(Im_2-I_{off})+I_{off}$$

Solving the above system of equations, β and $I_{off}$ are expressed by $$\beta=(Is_1-Is_2)/(Im_1-Im_2)$$

$$I_{off}=(Is_1-\beta Im_1)/(1-\beta)$$

The calculating portion 11 in this embodiment calculates the subtracted value sensitivity ratio β and the offset current $I_{off}$ using the above equations and stores them.

Figure 20:
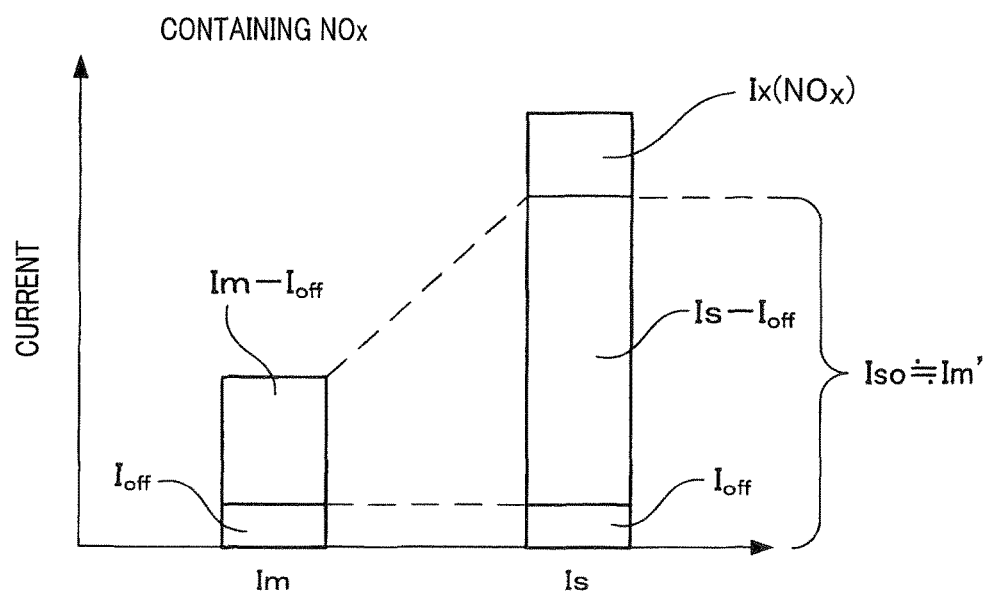
FIG. 20 is a graph which shows breakdowns of Im and Is when gas containing NOx is measured in the fourth embodiment.

When determining the concentration of NOx, the calculating portion 11, as illustrated in FIG. 20, measures the monitor cell current Im and the sensor cell current Is. The calculating portion 11 then corrects the measured value of the monitor cell current Im to bring it close to the value of the oxygen dependent current Iso using the following equation.

$$Im'=\beta(Im-I_{off})+I_{off}$$

Subsequently, the calculating portion 11 subtracts the corrected value Im' of the monitor cell current Im from the sensor cell current Is using an equation below to derive the given gas dependent current Ix.

$$Ix=Is-Im'=Is-\{\beta(Im-I_{off})+I_{off}\}$$

By the above operations, the given gas dependent current Ix is derived accurately to determine the concentration of the given gas component.

This embodiment offers the same arrangements and beneficial effects as those in the first embodiment.

Fifth Embodiment

This embodiment is an example where the gas g containing NOx is used to determine the approximate value β' of the subtracted value sensitivity ratio β and the approximate value $I_{off}'$ of the offset current $I_{off}$. The subtracted value sensitivity ratio β and the offset current $I_{off}$ usually change with time. After the gas concentration measuring apparatus 1 is installed in the automotive vehicle, there are few chances to measure the gas g which does not contain NOx. In this embodiment, the gas g containing NOx is, therefore, used to measure the approximate value β' of the subtracted value sensitivity ratio β and the approximate value $I_{off}'$ of the offset current $I_{off}$ at regular intervals and update them.

Figure 21:
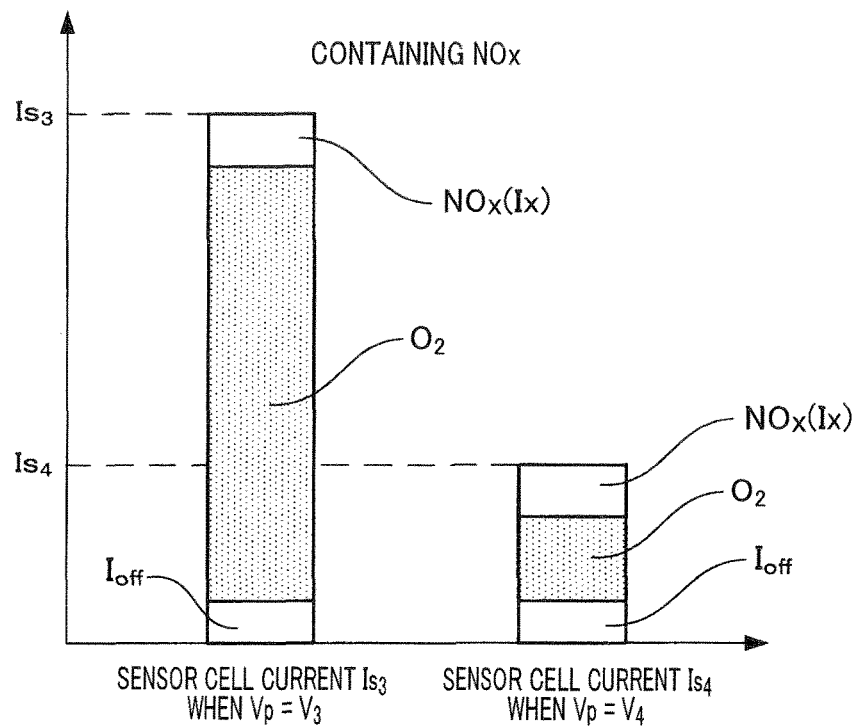
FIG. 21 is a graph which represents breakdowns of sensor cell currents $Im_3$ and $Is_4$ when a pump cell voltage is set to V3 or V4 in the fifth embodiment.

When measuring the approximate values β' and $I_{off}'$, a third voltage V3 and a fourth voltage V4 which are different in level from each other are applied to the pump cell 3. The sensor cell current $Is_3$ and the monitor cell current $Im_3$ when the third voltage V3 is applied (see FIGS. 21 and 22), and the sensor cell current $Is_4$ and the monitor cell current $Im_4$ when the fourth voltage V4 is applied are measured. The approximate values β' and $I_{off}'$ are calculated according to the following equation.

$$\beta'=(Is_3-Is_4)/(Im_3-Im_4) \quad (2)$$

$$I_{off}'=(Is_3-\beta'Im_3)/(1-\beta')$$

Figure 22:
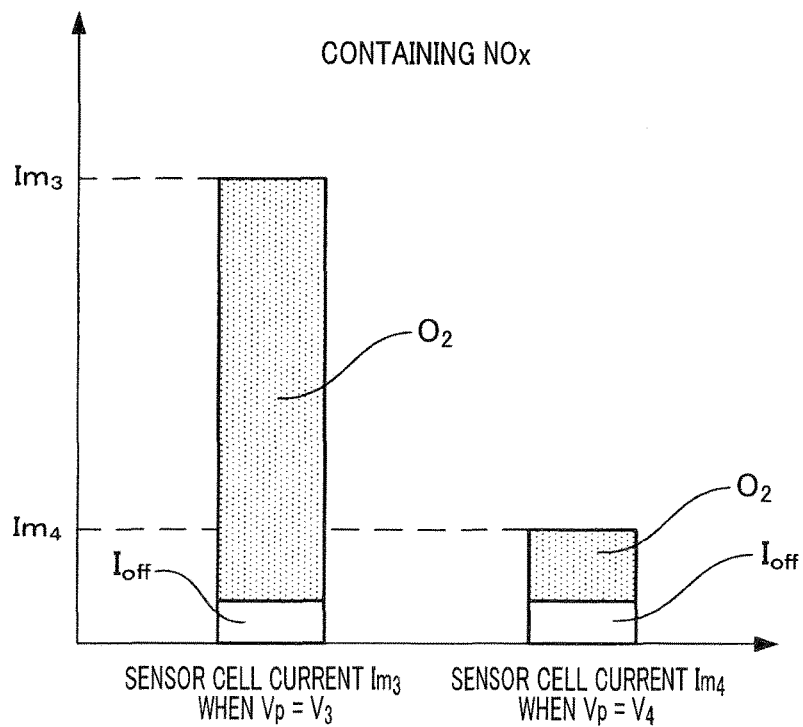
FIG. 22 is a graph which represents breakdowns of monitor cell currents $Im_3$ and $Im_4$ when a pump cell voltage is set to V3 or V4 in the fifth embodiment.

The values of the sensor cell current $Is_3$ and $Is_4$ are derived when the gas g has the same the concentration of the given gas component, so that values of the given gas dependent current Ix contained in the sensor cell current $Is_3$ and $Is_4$ are identical with each other. The values of the offset current $I_{off}$ are also identical with each other. In the numerator of the above equation (2), an operation of $Is_3-Is_4$ is made, so that Ix and $I_{off}$ will be eliminated. Similarly, as illustrated in FIG. 22, value of the offset current $I_{off}$ contained in the monitor cell currents $Im_3$ and $Im_4$ are the same. In the denominator of the above equation (2), an operation of $Im_3-Im_4$ is made, so that $I_{off}$ will be eliminated.

The use of the above equation (2) results in elimination of the offset current $I_{off}$ and the given gas dependent current Ix contained in each of the currents $Is_3$, $Is_4$, $Im_3$, and $Im_4$, thereby ensuring an enhanced accuracy in calculating the approximate value β' of the subtracted value sensitivity ratio β.

When measuring the concentration of the given gas component (NOx), the calculating portion 11 works to measure the sensor cell current Is and the monitor cell current Im and then correct the value of the monitor cell current Im according to an equation below to bring it close to the value of the oxygen dependent current Iso.

$$Im'=\beta'(Im-I_{off}')+I_{off}'$$

Subsequently, the calculating portion 11 uses an equation below to subtract the corrected value Im' of the monitor cell current Im from the sensor cell current Is to derive the approximate value Ix' of the given gas dependent current Ix and then uses the approximate value Ix' to determine the concentration of the given gas component.

$$Ix'=Is-Im'=Is-\{\beta'(Im-I_{off}')+I_{off}'\}$$

In the above way, the approximate values β' and $I_{off}$ which have been updated at regular intervals are used to calculate the approximate value Ix' of the given gas dependent current Ix, thereby resulting in an enhanced accuracy in determining the concentration of gas regardless of aging of the gas sensor 10.

This embodiment offers the same arrangements and beneficial effects as those in the first embodiment.

EXPLANATION OF REFERENCE SYMBOLS

1 gas concentration measuring apparatus
10 gas sensor
11 calculating portion
12 reference gas chamber
2 solid electrolyte body
3 pump cell
4 monitor cell
5 sensor cell
7 gas chamber
8 electrode
Im monitor cell current
Is sensor cell current
Iso oxygen dependent current
Ix given gas dependent current
g gas

The invention claimed is:

1. A gas concentration measuring apparatus which comprises a gas sensor exposed to gas and a calculating portion which uses an output from the gas sensor to calculate a concentration of a given gas component contained in the gas, characterized in that the gas sensor includes a gas chamber into which the gas is introduced, a reference gas chamber into which a reference gas is introduced, a solid electrolyte body which is disposed between the gas chamber and the reference gas chamber and has oxygen ion conductivity, and a plurality of electrodes disposed on both surfaces of the solid electrolyte body, in that the solid electrolyte body and the electrodes constitute a pump cell which works to regulate an oxygen concentration of the gas in the gas chamber, a monitor cell through which an amount of current corresponding to the oxygen concentration of the gas flows, and a sensor cell through which a current that is the sum of an amount of current corresponding to the oxygen concentration and an amount of current corresponding to a concentration of the given gas component in the gas flows, in that the calculating portion works to correct a value of a monitor cell current Im that is the current flowing through the monitor cell to bring it close to a value of an oxygen dependent current Iso which arises from an oxygen concentration and is a component of a sensor cell current Is that is the current flowing through the sensor cell and also subtract a corrected value Im' thereof from the sensor cell current Is to determine a given gas dependent current Ix that is a component of the sensor cell current Is which arises from the concentration of the given gas component to calculate the concentration of the given gas component in the gas, in that the calculating portion works to decrease voltage applied to the pump cell when the gas contains the given gas component to be lower than that when measuring the concentration of the given gas component and then measure, in such a condition, the sensor cell current Is and the monitor cell current Im to calculate, using an equation below, an approximate value a' of a sensitivity rate a that is a value derived by dividing the oxygen dependent current Iso by the monitor cell current Im $$Is/Im=a' \qquad (1)$$

and in that when measuring the concentration of the given gas component in the gas, the calculating portion measures the sensor cell current Is and the monitor cell current Im and calculates an approximate value Ix' of the given gas dependent current Ix using an equation below to approximately determine the concentration of the given gas component, $$Is-a'Im=Ix' \qquad (2).$$

2. A gas concentration measuring apparatus which comprises a gas sensor exposed to gas and a calculating portion which uses an output from the gas sensor to calculate a concentration of a given gas component contained in the gas, characterized in that the gas sensor includes a gas chamber into which the gas is introduced, a reference gas chamber into which a reference gas is introduced, a solid electrolyte body which is disposed between the gas chamber and the reference gas chamber and has oxygen ion conductivity, and a plurality of electrodes disposed on both surfaces of the solid electrolyte body, in that the solid electrolyte body and the electrodes constitute a pump cell which works to regulate an oxygen concentration of the gas in the gas chamber, a monitor cell through which an amount of current corresponding to the oxygen concentration of the gas flows, and a sensor cell through which a current that is the sum of an amount of current corresponding to the oxygen concentration and an amount of current corresponding to a concentration of the given gas component in the gas flows, in that the calculating portion works to correct a value of a monitor cell current Im that is the current flowing through the monitor cell to bring it close to a value of an oxygen dependent current Iso which arises from an oxygen concentration and is a component of a sensor cell current Is that is the current flowing through the sensor cell and also subtract a corrected value Im' thereof from the sensor cell current Is to determine a given gas dependent current Ix that is a component of the sensor cell current Is which arises from the concentration of the given gas component to calculate the concentration of the given gas component in the gas, in that when the gas contains the given gas component, the calculating portion applies a first voltage (V1) and a second voltage (V2) which have values different from each other to the pump cell and measures the monitor cell current $Im_1$ and the sensor cell current $Is_1$ when the first voltage (V1) is applied and the monitor cell current $Im_2$ and the sensor cell current $Is_2$ when the second voltage (V2) is applied to calculate, using an equation below, an approximate value a' of a sensitivity rate a that is a value derived by dividing the oxygen dependent current Iso by the monitor cell current Im $$(Is_1-Is_2)/(Im_1-Im_2)=a' \tag{3}$$

and in that when measuring the concentration of the given gas component in the gas, the calculating portion measures the sensor cell current Is and the monitor cell current Im and calculates an approximate value Ix' of the given gas dependent current Ix using an equation below to approximately determine the concentration of the given gas component, $$Is-a'Im=Ix' \tag{4}$$

3. A gas concentration measuring apparatus which comprises a gas sensor exposed to gas and a calculating portion which uses an output from the gas sensor to calculate a concentration of a given gas component contained in the gas, characterized in that the gas sensor includes a gas chamber into which the gas is introduced, a reference gas chamber into which a reference gas is introduced, a solid electrolyte body which is disposed between the gas chamber and the reference gas chamber and has oxygen ion conductivity, and a plurality of electrodes disposed on both surfaces of the solid electrolyte body, in that the solid electrolyte body and the electrodes constitute a pump cell which works to regulate an oxygen concentration of the gas in the gas chamber, a monitor cell through which an amount of current corresponding to the oxygen concentration of the gas flows, and a sensor cell through which a current that is the sum of an amount of current corresponding to the oxygen concentration and an amount of current corresponding to a concentration of the given gas component in the gas flows, in that the calculating portion works to correct a value of a monitor cell current Im that is the current flowing through the monitor cell to bring it close to a value of an oxygen dependent current Iso which arises from an oxygen concentration and is a component of a sensor cell current Is that is the current flowing through the sensor cell and also subtract a corrected value Im' thereof from the sensor cell current Is to determine a given gas dependent current Ix that is a component of the sensor cell current Is which arises from the concentration of the given gas component to calculate the concentration of the given gas component in the gas, in that when the gas contains the given gas component, the calculating portion increases voltage applied to the pump cell to be higher than that when calculating the concentration of the given gas component and then measure, in such a condition, the sensor cell current Is and the monitor cell current Im to calculate, using an equation below, an approximate value a' of a sensitivity rate a that is a value derived by dividing the oxygen dependent current Iso by the monitor cell current Im $$Is/Im=a' \tag{5}$$

and in that when measuring the concentration of the given gas component in the gas, the calculating portion measures the sensor cell current Is and the monitor cell current Im and calculates an approximate value Ix' of the given gas dependent current Ix using an equation below to approximately determine the concentration of the given gas component, $$Is-a'Im=Ix' \tag{6}$$

4. A gas measuring apparatus as set forth in claim 1, characterized in that the gas chamber is integrally formed to have a space which is entirely constant in a thickness-wise direction of the solid electrolyte body and also in a width-wise direction perpendicular to both a direction of flow of the gas and the thickness-wise direction from where the pump cell is formed to where the monitor cell and the sensor cell are formed.

5. A gas measuring apparatus as set forth in claim 1, characterized in that the single solid electrolyte body is shared among the pump cell, the monitor cell, and the sensor cell.

* * * * *